US012337145B2

(12) United States Patent
Müller (10) Patent No.: US 12,337,145 B2
(45) Date of Patent: Jun. 24, 2025

(54) DRIVE MECHANISM FOR A MEDICAMENT DELIVERY DEVICE

(71) Applicant: SHL MEDICAL AG, Zug (CH)

(72) Inventor: Stephan Müller, Hemishofen (CH)

(73) Assignee: SHL Medical AG, Zug (CH)

( * ) Notice: Subject to any disclaimer, the term of this patent is extended or adjusted under 35 U.S.C. 154(b) by 890 days.

(21) Appl. No.: 17/612,076

(22) PCT Filed: May 22, 2020

(86) PCT No.: PCT/EP2020/064275
§ 371 (c)(1),
(2) Date: Nov. 17, 2021

(87) PCT Pub. No.: WO2020/249373
PCT Pub. Date: Dec. 17, 2020

(65) Prior Publication Data
US 2022/0203030 A1    Jun. 30, 2022

(30) Foreign Application Priority Data
Jun. 12, 2019 (EP) .................................... 19179659

(51) Int. Cl.
*A61M 5/20* (2006.01)
*A61M 5/145* (2006.01)
*A61M 5/32* (2006.01)

(52) U.S. Cl.
CPC ........ *A61M 5/2033* (2013.01); *A61M 5/3204* (2013.01); *A61M 2005/14533* (2013.01);
(Continued)

(58) Field of Classification Search
CPC .............. A61M 5/2033; A61M 5/3204; A61M 5/31583; A61M 5/1454; A61M 5/31586;
(Continued)

(56) References Cited

FOREIGN PATENT DOCUMENTS

| EP | 2698180 A1 | 2/2014 |
|----|------------|--------|
| GB | 2552340 A  | 1/2018 |

(Continued)

OTHER PUBLICATIONS

International Search Report and Written Opinion for Int. App. No. PCT/EP2020/064275, mailed Jun. 9, 2020.

*Primary Examiner* — Michael J Tsai
*Assistant Examiner* — Forrest Blake Dipert
(74) *Attorney, Agent, or Firm* — McDonnell Boehnen Hulbert & Berghoff LLP (57) ABSTRACT

A drive mechanism for a medicament delivery device is presented having a base member with a guide track structure that includes a first track, a second track, a rotator base member having a first guide structure that runs in the first track, a rotator housing coaxially arranged with and configured to engage with the rotator base member, the rotator housing having a second guide structure arranged at a fixed distance from the first guide structure and configured to run in the second track, a rotation device configured to actuate the rotator housing, and a medicament container carrier configured to receive a medicament container, wherein the medicament container carrier is coaxially arranged relative to the rotator base member and the rotator housing, the rotator housing being configured to rotate relative to the medicament container carrier.

20 Claims, 6 Drawing Sheets (52) U.S. Cl.
CPC .............. *A61M 2005/2026* (2013.01); *A61M 2005/208* (2013.01); *A61M 2205/103* (2013.01)

(58) Field of Classification Search
CPC .... A61M 2005/2026; A61M 2005/208; A61M 2005/103; A61M 2005/206; A61M 2005/14533; A61M 2005/2485; A61M 2005/2477; A61M 2005/3152; A61M 2005/2073; A61M 2205/103
See application file for complete search history.

(56) References Cited

FOREIGN PATENT DOCUMENTS

| | | | | |
|---|---|---|---|---|
| WO | WO-2009081132 A1 | * | 7/2009 | .......... A61M 5/2033 |
| WO | 2017/187177 A1 | | 11/2017 | |

* cited by examiner

DRIVE MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2020/064275 filed May 22, 2020, which claims priority to European Patent Application No. 19179659.8 filed Jun. 12, 2019. The entire disclosure contents of these applications are herewith incorporated by reference into the present application.

TECHNICAL FIELD

The present disclosure generally relates to medicament delivery devices, and particularly to automatic medicament delivery devices.

BACKGROUND

More compact medicament delivery devices have been developed recently. These medicament delivery devices do typically not rely on the usual coaxial configuration of internal drive components such as e.g. a piston rod used for conventional medicament delivery devices of an elongated pen-like shape such as auto-injectors. Instead, these medicament delivery devices may utilise balls or beads arranged in a curved channel, which are moved into the medicament container to cause medicament expelling.

An example of a medicament delivery device of the above-described type is disclosed in WO2017/187177 A1. This document discloses a medicament delivery device for the delivery of medicament from a container through a cannula. The device comprises a chassis, a carriage, and an insertion spring for biasing the carriage for movement in an insertion direction with respect to the chassis from a starting position in which the cannula is shrouded to an insertion position in which the cannula is extended. A drive mechanism is provided for driving the container's stopper to expel medicament. The drive mechanism is carried by the carriage and comprises a movable drive member, a drive means for applying a driving force to the drive member, and force transmission means for transmitting the driving force to the stopper. The drive means is arranged around or alongside at least part of the force transmission means.

The design of the medicament delivery device disclosed in WO2017/187177 A1 is relatively complicated. Moreover, there is a risk that a user gets stung by the cannula after medicament administration.

SUMMARY

An object of the present disclosure is to provide a drive mechanism for a medicament delivery device which solves or at least mitigates problems of the prior art.

There is hence according to a first aspect of the present disclosure provided a drive mechanism for a medicament delivery device, comprising: a base member having a guide track structure, the guide track structure including a first track, and a second track, a rotator base member having a first guide structure configured to run in the first track, a rotator housing coaxially arranged with and configured to engage with the rotator base member, the rotator housing having a second guide structure arranged at a fixed distance from the first guide structure and configured to run in the second track, a rotation device configured to actuate the rotator housing, and a medicament container carrier configured to receive a medicament container, wherein the medicament container carrier is coaxially arranged relative to the rotator base member and the rotator housing, the rotator housing being configured to rotate relative to the medicament container carrier, wherein the first track and the second track are arranged relative to each other such that actuation of the rotator housing causes the second guide structure to move along the second track and the first guide structure to initially move in a first direction along the first track and subsequently to move in a second direction opposite to the first direction, the movement of the first guide structure in the first direction causing initial linear movement of the medicament container carrier in the first direction, the movement of the first guide structure in the second direction causing subsequent movement of the medicament container carrier in the second direction, and movement of the second guide structure causing rotation of the rotator housing, thereby enabling a medicament delivery. The track portion can be defined by e.g. a groove, a slit or a wall (not shown).

A compact drive mechanism is thereby provided which by means of the linear movement in the first and second direction along its longitudinal axis $15a$ provides auto-penetration and auto-withdrawal functionality in a simple manner. A delivery member, such as a needle or cannula, will therefore not be exposed either before or after medicament administration. The rotating motion of the medicament container carrier furthermore enables initiation/activation functionality of medicament administration.

The first track may for example be a straight track or an elongated track. In case the first track is elongated, it may for example be undulating and/or slightly curved such as J- or C-shaped.

The first track may be configured to enable linear or generally linear movement of the medicament container carrier and rotator housing relative to the base member.

The second track may be a curved track.

The second track may be configured to enable rotation of the rotator housing relative to the base.

According to one embodiment the second track has an arced portion, a first straight portion and a second straight portion, the arced portion connecting the first straight portion and the second straight portion, wherein the first track and the second track are arranged relative to each other such that said movement of the second guide structure along the second track comprises three phases A-C:

A) when the first guide structure is moved in the first direction from an initial position to a temporary position along the first track, the second guide structure is configured to move along the first straight portion towards the arced portion, B) when the second guide structure reaches the arced portion, the second guide structure is configured to move along the arced portion towards the second straight portion, wherein the first guide structure maintains its temporary position, causing rotation of the rotator housing, and C) when the second guide structure reaches the second straight portion, the first guide structure is configured to move in the second direction from the temporary position to the initial position along the first track and the second guide structure is configured to move along the second straight portion away from the arced portion, causing the medicament container carrier to move in the second direction.

This configuration of the second track and its arrangement relative to the first track provides the automatic injection and the auto-withdrawal of the container carrier with the container and its needle, and medicament delivery functionality in a simple manner.

By actuation of the rotator housing by the rotation device, the second guide structure is forced to move along the first straight portion and the first guide structure is forced to move in the first direction along the first track, from the initial position to the temporary position. These motions are obtained due to the actuation of the rotator housing, the configuration of the first track and the second track, and due to the fixed distance between the first guide structure and the second guide structure. When the second guide structure has reached a position where the first straight portion transitions into the arced portion, the rotator housing is further rotated as the second guide structure runs in the arced portion. The first guide structure maintains its position in the temporary position while the second guide structure runs in the arced portion. When the second guide structure has reached a position where the arced portion transitions into the second straight portion, the second guide structure is moved into the second straight portion. Concurrently with the movement of the second guide structure in the second straight portion, the first guide structure moves from the temporary position to the final position in the first track.

During the above-described three phases or stages A-C, the medicament container carrier is hence initially moved linearly in the first direction, providing an auto-penetration motion, and subsequently moved linearly in the second direction, providing an auto-withdrawal motion. The rotation of the rotator housing relative to the medicament container carrier, between these two linear movements, enables medicament administration.

The rotation of the rotator housing is generally performed both during linear movement of the first guide structure in the first direction and in the second direction, and between these movements of the first guide structure.

The rotation of the rotator housing is performed around the rotator base member.

According to one embodiment the base member has a proximal end and a distal end and a central longitudinal axis extending between the proximal end and the distal end, wherein the first track extends parallel with the central longitudinal axis.

According to one embodiment the first straight portion and the second straight portion extend radially inwards from the arced portion, the first straight portion and the second straight portion being arranged opposite to each other.

According to one embodiment the arced portion is arranged distally relative to the first track, partially enclosing the first track, wherein the first straight portion and the second straight portion extend towards the first track from opposing sides.

According to one embodiment the first track and the second track are disjoint tracks.

According to one embodiment the rotation device is a clock spring.

The clock spring may be connected to the base member and to the rotator housing.

One embodiment comprises a movable trigger mechanism, wherein in an initial state of the drive mechanism, the trigger mechanism is configured to prevent the rotation device from rotating the rotator housing.

According to one embodiment movement of the trigger mechanism is configured to release the rotator housing, enabling the rotator housing to be actuated by the rotation device.

According to one embodiment the rotation device comprises a motor and a planetary gear train configured to actuate the rotator housing.

One embodiment comprises a plurality of beads, wherein the medicament container carrier has a channel having a straight channel portion and a curved channel portion leading into the straight channel portion, the straight channel portion being configured to receive a medicament container, the beads being arranged one after the other in the curved channel portion.

According to one embodiment the rotator housing has a protrusion extending into the curved channel portion and arranged at one end of the beads, wherein rotation of the rotator housing relative to the medicament container carrier causes the protrusion to move the beads in the curved channel portion into the straight channel portion.

There is according to a second aspect of the present disclosure provided a medicament delivery device comprising the drive mechanism according to the first aspect.

According to one embodiment the base member forms a first housing part of the medicament delivery device.

One embodiment comprises a pre-filled medicament container with a medicament delivery member covered by a protective shield and a cap with a delivery member shield remover.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction if the longest extension of the device and/or component.

Similarly, the terms "radial", "transversal" or "orthogonal" refers to a direction generally perpendicular to the longitudinal direction which is the axis direction and e.g. "radially or orthogonally outward" will refer to a direction pointing away for the longitudinal axis.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
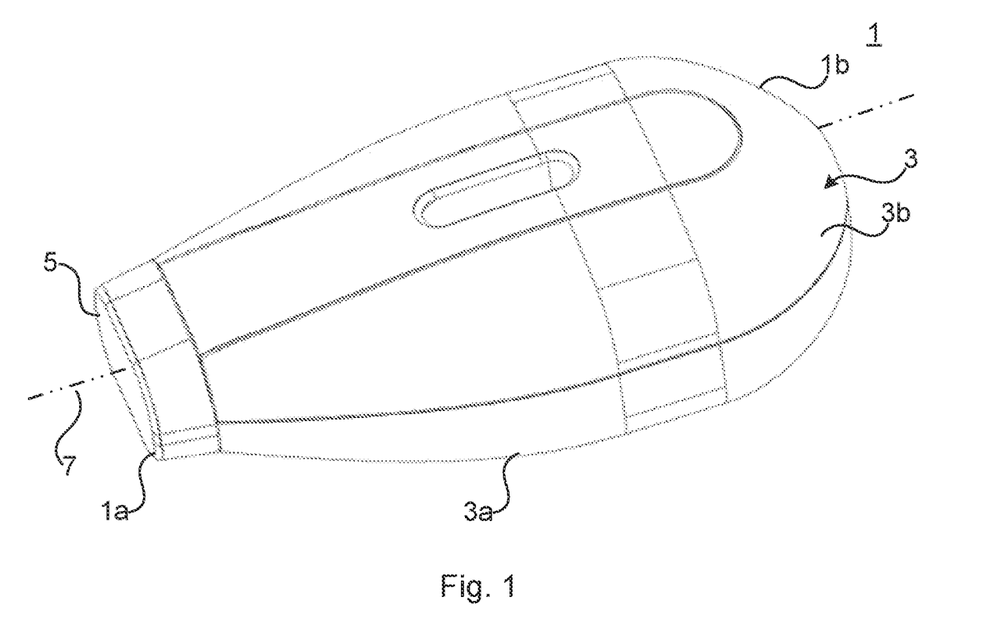
FIG. 1 is a perspective view of an example of a medicament delivery device.

FIG. 1 is a perspective view of an example of a medicament delivery device 1. The exemplified medicament delivery device 1 is an auto-injector.

The medicament delivery device 1 comprises a housing 3. The housing 3 comprises a first housing part 3a, which may be a lower housing part, and a second housing part 3b, which may be an upper housing part. The second housing part 3b will in the following be referred to as base member 3b.

The medicament delivery device 1 has a proximal end 1a and a distal end 1b. The proximal end 1a is configured to face the injection site during injection. The distal end is arranged opposite to the proximal end 1b. The medicament delivery device 1 and the base member 3a has a central longitudinal axis 7 which extends between the proximal end 1a and the distal end 1b. The proximal direction is defined along the central longitudinal axis 7 in a direction from the distal end 1b towards the proximal end 1a. The distal direction is defined along the central longitudinal axis 7 in a direction from the proximal end 1a towards the distal end 1b.

The exemplified medicament delivery device 1 comprises a cap 5. The cap 5 is configured to cover a proximal opening of the housing 3 and protects the internal components of the medicament delivery device 1.

Figure 2:
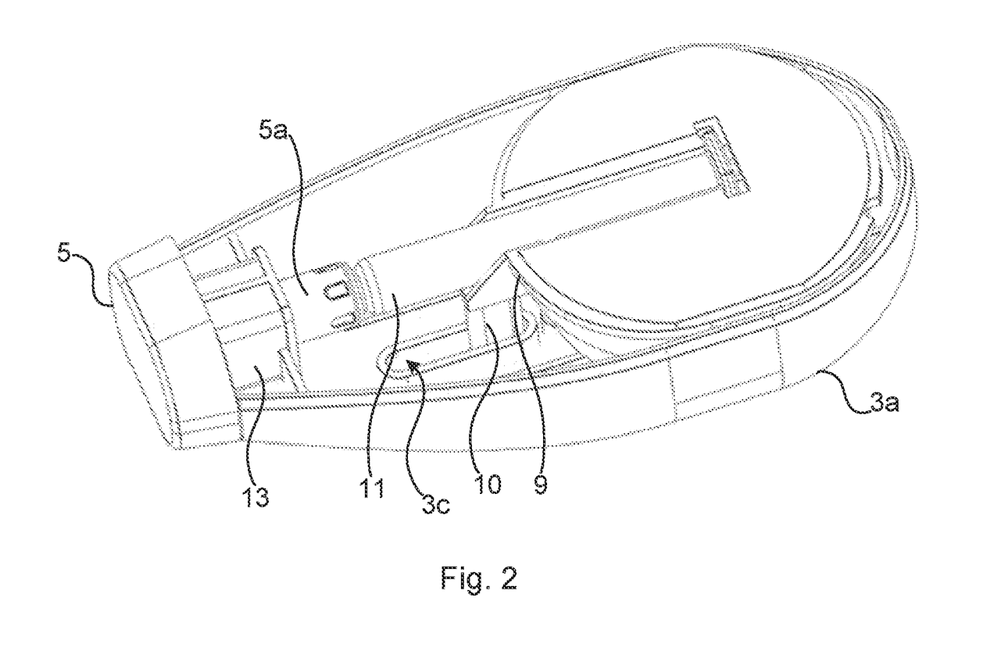
FIG. 2 is a perspective view of the medicament delivery device shown in FIG. 1 with part of the housing removed.

FIG. 2 is a perspective view of the medicament delivery device 1 with the second housing part 3b removed to expose the interior of the medicament delivery device 1. The medicament delivery device 1 comprises a medicament container carrier 9, a medicament container 11, and a stopper or a plunger 18 configured to be arranged inside the medicament container 11. The medicament container 11 comprises a delivery member such as a needle (not shown in FIG. 2). The medicament container carrier 9 is configured to receive or hold the medicament container 11. The medicament container carrier 9 is configured to move between a default position shown in FIG. 2 and a proximal position relative to the first housing part or a base member 3a.

The medicament container carrier 9 has a guide protrusion 10. The base member 3a has an inner surface provided with a guide slot 3c. The guide protrusion 10 is configured to run in the guide slot 3c. The guide slot 3c and the guide protrusion 10 ensure that the medicament container carrier 9 moves along the central longitudinal axis 7 when moved between the default position and the proximal position.

The cap 5 has a delivery member shield remover 5a. The delivery member 11a is protected by a protective delivery member shield 14 (both shown in FIG. 3) arranged radially inside the delivery member shield remover 5a.

The exemplified medicament delivery device 1 comprises a trigger 13. The trigger 13 is exposed when the cap 5 is removed. The trigger 13 is configured to be moved linearly into the housing 3, i.e. in the distal direction, to activate a medicament delivery.

Figure 3:
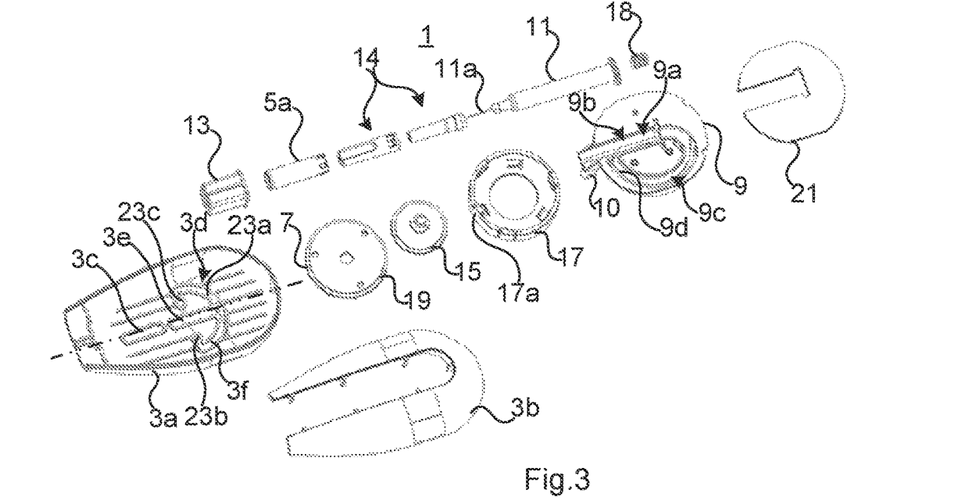
FIG. 3 is an exploded view of the medicament delivery device in FIG. 1.

FIG. 3 shows an exploded view of the medicament delivery device 1, with most of its components visible. The medicament delivery device 1 comprises a rotator base member 15, a rotator housing 17, and a rotator cover 19. The exemplified medicament delivery device 1 comprises a medicament container carrier cover 21 configured to be mounted to the medicament container carrier 9.

The medicament delivery device 1 also comprises a rotation device (not shown). The rotation device may for example be a clock spring or an assembly of an electric motor and a planetary gear train. The rotation device is configured to actuate the rotator housing 17 causing the rotator housing 17 to rotate. The rotator housing 17 is configured to house the rotation device. For example, the clock spring may be coiled inside the rotator housing 17. In an example in which the rotation device is a clock spring, the clock spring may be connected to the rotator housing 17 and to the rotator base member 15 to rotationally bias the rotator housing 17 relative to the rotator base member 15. In an example in which the rotation device comprises an electric motor (not shown), the rotor of the motor may be arranged along the central axis of the rotator housing 17. The planetary gear train (not shown) may mechanically connect the rotor of the electric motor with the inner surface of the rotator housing 17 to enable actuation of the rotator housing 17 by means of the electric motor.

The rotator base member 15, the rotator housing 17 and the medicament container carrier 9 form part of a drive mechanism.

The base member 3a has a guide track structure 3d. The guide track structure 3d is provided on an inner surface of the base member 3a, i.e. the first housing part. The guide track structure 3d comprises a first track 3e and a second track 3f. The first track 3e and the second track 3f may be disjoint tracks. The first track 3e and the second track 3f may hence be physically separate tracks.

The first track 3e may be a straight track or an elongated track, for example an undulating elongated track, or a slightly curved elongated track.

The second track 3f may be a curved track.

The first track 3e is arranged parallel with the central longitudinal axis 7. In the present example, the first track 3e coincides with the central longitudinal axis 7. The second track 3f is arranged distally relative to the first track 3e. The second track 3f partially encloses the straight track 3e. The first track 3e and the second track 3f are arranged symmetrically with respect to the central longitudinal axis 7.

The exemplified second track 3f includes an arced portion 23a, a first straight portion 23b and a second straight portion 23c. The arced portion 23a is arranged distally relative to the first track 3e. The arced portion 23a connects the first straight portion 23b and the second straight portion 23c. The first straight portion 23b and the second straight portion 23c are arranged opposite to each other and extend towards each other. The first straight portion 23b and the second straight portion extend towards the first track 3e from opposite sides. The first track 3e is arranged between the first straight portion 23b and the second straight portion 23c. The first straight portion 23b and the second straight portion 23c are arranged aligned or essentially aligned with each other. The first straight portion 23b and the second straight portion 23c are arranged perpendicular to the longitudinal extension of the first track 3e.

The rotator base member 15 is configured to engage with the first track 3e. The rotator housing 17 is configured to be arranged coaxially with the rotator base member 15. The rotator housing 17 is configured to engage with the rotator base member 15. The rotator housing 17 and the rotator base member 15 are configured to engage such that they are able to move linearly concurrently. The rotator housing 17 is configured to be able to rotate relative to the rotator base member 15. The rotator housing 17 is configured to engage with the second track 3f.

The rotator cover 19 is configured to be mounted coaxially to the rotator housing 17. The medicament container carrier 9 is configured to be mounted coaxially to the rotator cover 19. The rotator housing 17 is configured to rotate relative to the medicament container carrier 9.

The medicament container carrier 9 has a channel 9a. The channel 9a has a straight channel portion 9b configured to receive the medicament container 11. The channel 9a has a curved channel portion 9c leading into the straight channel portion 9b. The medicament delivery device 1 also comprises a plurality of beads or balls (not shown). The beads are configured to be arranged one after the other in the curved channel portion 9c. The curved channel portion 9c has a floor or lower surface provided with a slit 9d that extends along the curved channel portion 9c. The rotator housing 17 has a protrusion 17a which is configured to extend into the curved channel portion 9c via the slit 9d. In an initial state of the medicament delivery device 1, the protrusion 17a is arranged at an end of the curved channel portion 9c, behind the beads. When the rotator housing 17 is actuated by the rotation device, causing rotation of the rotator housing 17, the protrusion 17a will move along the slit 9d and move the beads towards the straight channel portion 9b and into the medicament container 11 arranged in the straight channel portion 9b. In this manner, medicament delivery is provided.

Figure 4:
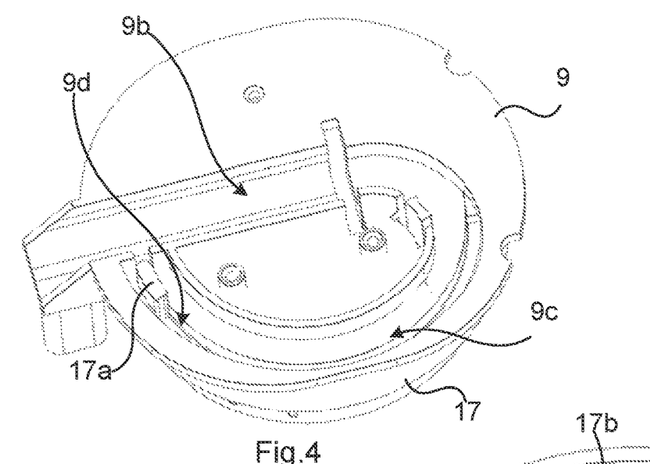
FIG. 4 is a perspective view of certain parts of an example of a drive mechanism.

FIG. 4 shows when the rotator housing 17 is assembled with the medicament container carrier 9, in the initial state of the medicament delivery device 1. As can be seen, the protrusion 17a is arranged in the curved channel portion 9c.

Figure 5:
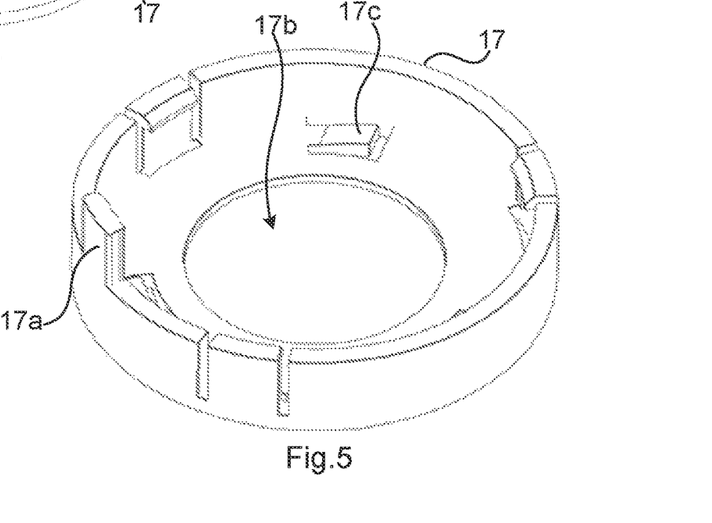
FIG. 5 is a perspective view of an example of a rotator housing.

FIG. 5 depicts a perspective top view of the rotator housing 17. The rotator housing 17 is cylindrical or essentially cylindrical. The rotator housing 17 is provided with a central through-opening 17b configured to receive a portion of the rotator base member 15. The protrusion 17a extends from an upper edge of the rotator housing 17, towards the medicament container carrier 9. The exemplified rotator housing 17 has an inner surface provided with a plurality of flexible tabs 17c. The flexible tabs 17c in conjunction with ribs on the lower face of rotator cover 19 facilitate the coiling of the clock spring during assembly of the medicament delivery device 1.

Figure 6:
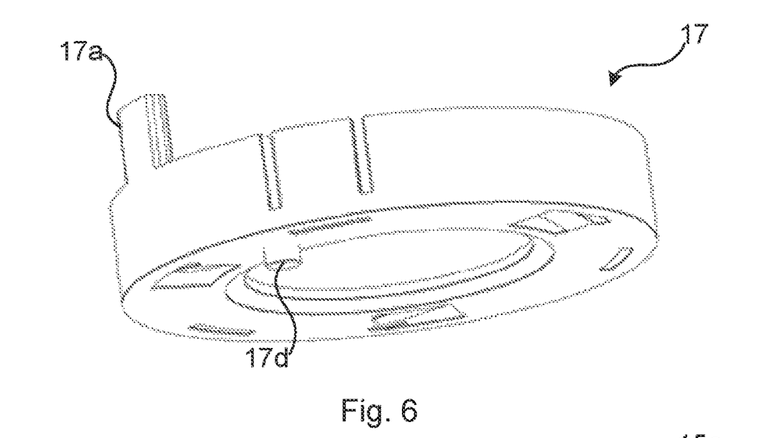
FIG. 6 is another perspective view of the rotator housing in FIG. 5.

FIG. 6 depicts a perspective bottom view of the rotator housing 17. The rotator housing 17 has a guide structure 17d, in the following referred to as a second guide structure 17d. The second guide structure 17d is configured to engage with the second track 3f. The second guide structure 17d is configured to run in the second track 3f. The second guide structure 17d may be a pin or a protrusion which extends from a bottom side of the rotator housing 17 towards the base member 3a.

Figure 7:
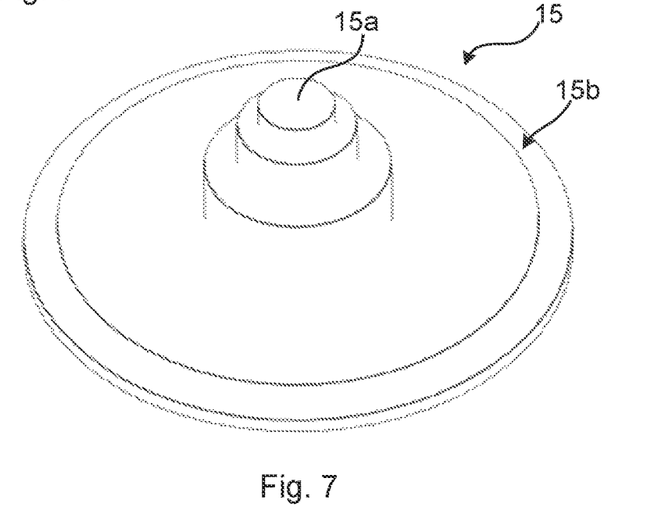
FIG. 7 is a perspective view of an example of a rotator base.

FIG. 7 shows a perspective top view of the rotator base member 15. The rotator base member 15 is circular or essentially circular. The rotator base member 15 has an engagement structure 15a configured to engage with the rotator cover 19. The engagement structure 15a may be a central axial protrusion configured to be received by a corresponding central opening in the rotator cover 19. The rotator base member 15 has a circumferentially extending flange structure 15b, which provides a connection with the rotator housing 17 via the central through-opening 17b.

Figure 8:
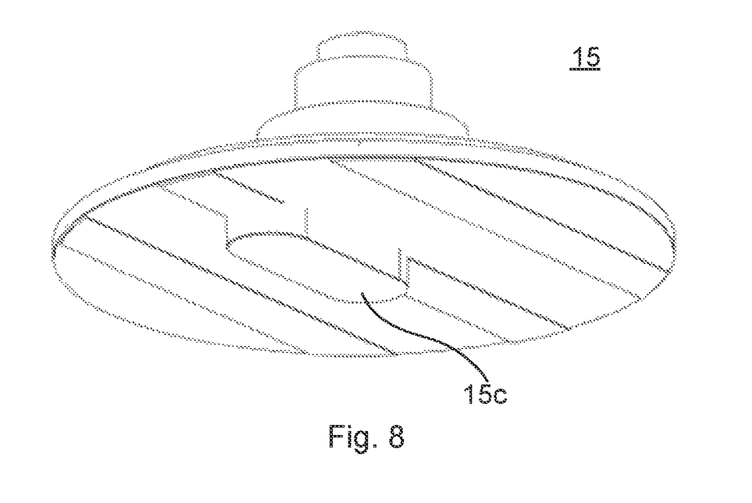
FIG. 8 is another perspective view of the rotator base in FIG. 7.

FIG. 8 shows a perspective bottom view of the rotator base member 15. The rotator base comprises a guide structure 15c, in the following referred to as the first guide structure 15c. The first guide structure 15c is configured to engage with the first track 3e. The first guide structure 15c is configured to run in the first track 3e. According to the example in FIG. 8 the first guide structure 15c is arranged offset from the centre of the rotator base member 15.

The first guide structure 15c is arranged at a fixed distance from the second guide structure 17d. The second guide structure 17d is arranged radially outside of the first guide structure 15c.

The operation of the medicament delivery device 1 will now be described with reference to FIGS. 9-13.

Figure 9:
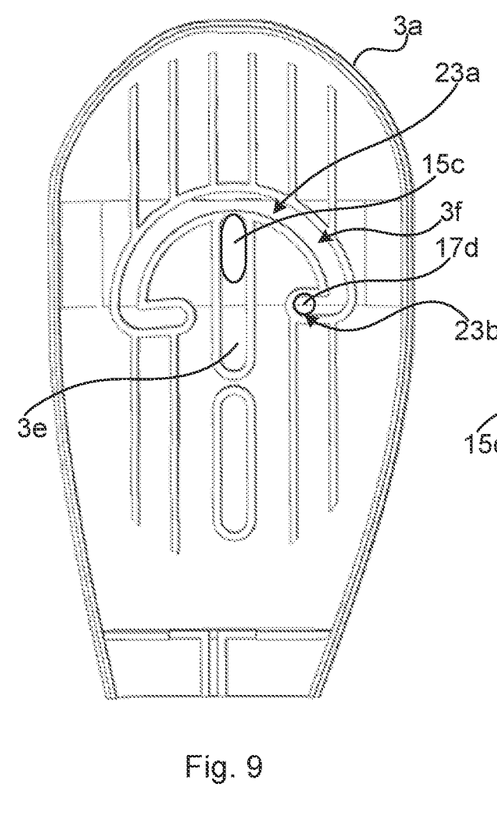
FIG. 9 depicts positions of a first guide structure and a second guide structure in a guide track structure in an initial state of the medicament delivery device.

In the initial state of the medicament delivery device 1, the cap 5 is mounted to the proximal end of the housing 3. When a user is to perform a medicament delivery, the cap 5 is removed from the housing 3. The protective delivery member shield 14 is thereby removed from the delivery member, exposing the delivery member 11a which is still arranged inside the housing 3. The trigger 13 is exposed by removal of the cap 5. The trigger 13 forms part of a triggering mechanism which enables actuation of the rotator housing 17.

The user can now push the medicament delivery device 1 towards the site of injection with the trigger 13 bearing against the site of injection. When the trigger 13 is moved into the housing 3, i.e. in the distal direction, the triggering mechanism releases the rotator housing 17, which is initially prevented from rotation. If the rotation device is a clock spring, the triggering mechanism may for example comprise notch provided in e.g. the rotator housing 17, and a rigid member such as a rod or wire which is connected to the trigger 13 and extends into the notch to prevent rotation of the rotator housing 17 as long as the trigger 13 is in its initial trigger position. When the trigger 13 is moved in the distal direction, the rotator housing 17 is released. If the rotation device comprises a motor, the trigger 13 may be configured to power up the electric motor, causing rotation of the rotator housing 17.

FIG. 9 depicts the position of the first guide structure 15c and the second guide structure 17d in the initial state of the medicament delivery device 1. The cap 5 may or may not have been removed from the housing 3. The first guide structure 15c is arranged in the first track 3e and the second guide structure 17d is arranged in the second track 3f. In particular, the first guide structure 15c is arranged in a first position in the first track 3e. The first position is in a distal portion of the first track 3e. The second guide structure 17d is arranged in the first straight portion 23b of the second track 3f, at an end of the first straight portion 23b being most distant from the arced portion 23a.

Figure 10:
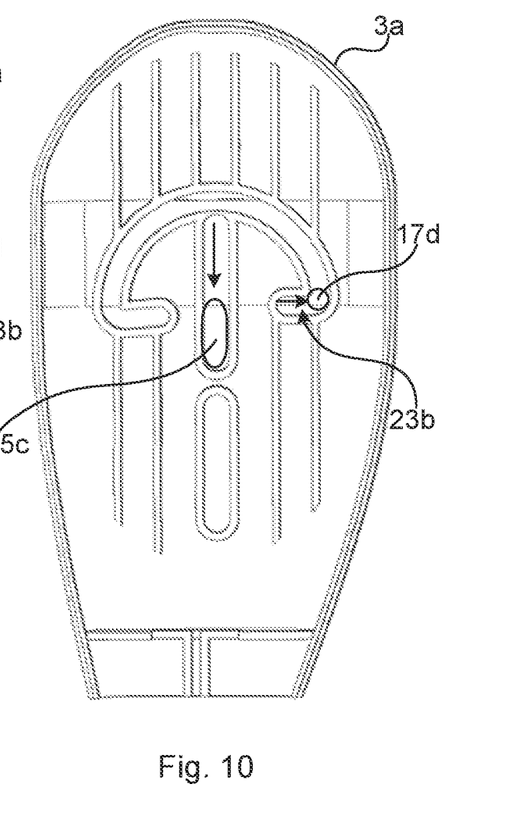
FIG. 10 depicts the positions of the first guide structure and the second guide structure during auto-penetration of a delivery member.

In FIG. 10, the cap 5 has been removed and the trigger 13 has been moved in the distal direction into the housing 3. A medicament delivery procedure has hence commenced. The movement of the trigger 13 causes the release of the rotator housing 17. The rotation device is thereby able to actuate the rotator housing 17. As a result, in a phase A), the second guide structure 17d is moved along the first straight portion 23b towards the arced portion 23a, and the first guide structure 15c is moved in the proximal direction along the straight track 3e to a proximal end of the first track 3e to obtain a temporary position. Due to this initial movement of the first guide structure 15c and the second guide structure 17d, the rotator base member 15, the rotator housing 17, the rotator housing cover 19 and the medicament container carrier 9 are moved linearly in the proximal direction. The rotator housing 17 is slightly rotated during this linear movement. Since the medicament container 11 is held by the medicament container carrier 9, the medicament container 11 and the delivery member 11a are moved towards the proximal opening of the housing 3. The delivery member 11a moves through the proximal opening. The delivery member 11a therefore penetrates the injection site. Auto-penetration functionality is hence provided.

Figure 11:
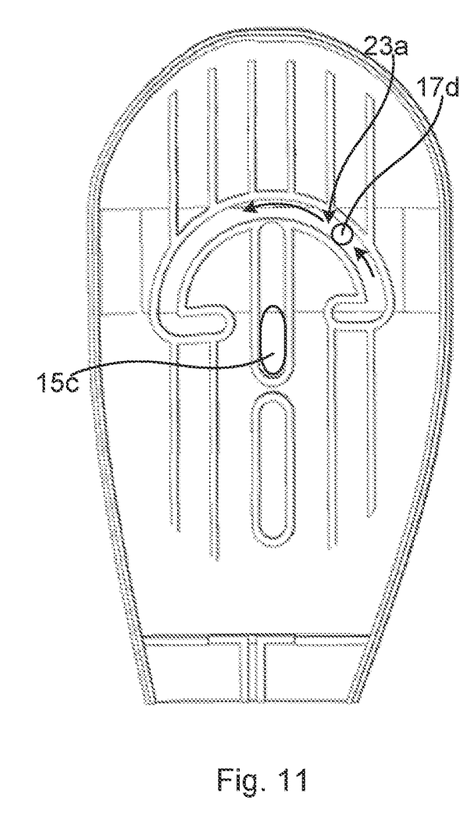
FIG. 11 depicts the positions of the first guide structure and the second guide structure during medicament delivery.

FIG. 11 depicts the continued movement of the second guide structure 17d as it has moved from the first straight portion 23b into the arced portion 23a and moves along the arced portion 23a, in a phase B). This movement of the second guide structure 17d causes rotation of the rotator housing 17 relative to the base member 3a and the medicament container carrier 9. The protrusion 17a will thereby move along the slit 9d of the curved channel portion 9c of the medicament container carrier 9. The beads are thus moved along the curved channel portion 9c into the straight channel portion 9b, pushing the plunger 18 further into the medicament container 11. Medicament delivery is thereby provided through the delivery member 11a which at this point has penetrated the site of injection. The first guide structure 15c is maintained in the temporary position and hence the delivery member 11a is maintained in its penetrated position at the injection site.

Figure 12:
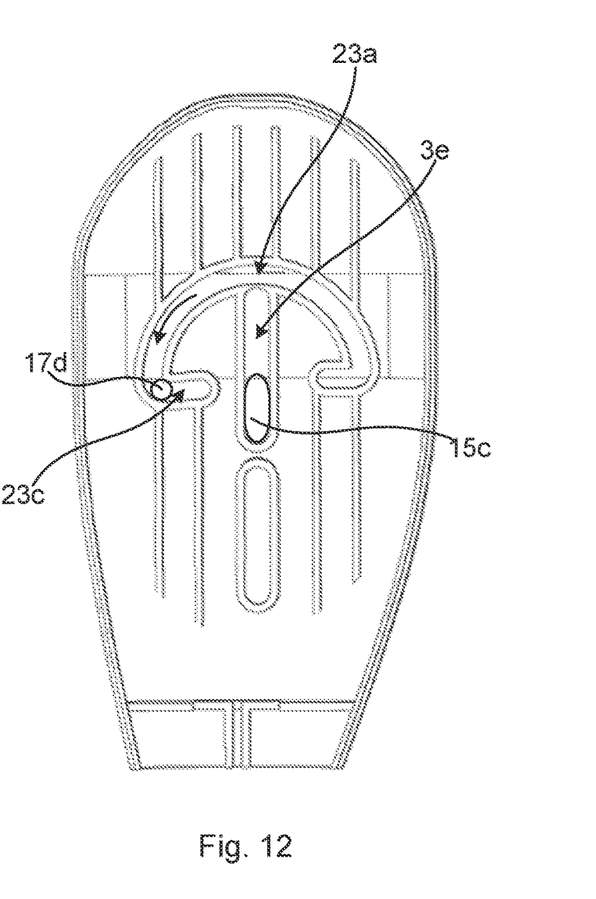
FIG. 12 depicts the positions of the first guide structure and the second guide structure when medicament delivery is being finalised.

FIG. 12 depicts when the second guide structure 17d has reached the end of the arced portion 23a and is about to move into the second straight portion 23c which extends from the end of the arced portion 23a. The first guide structure 15c is still in the temporary position in the first track 3e. At this point, the protrusion 17a has moved its full motion or stroke in the curved channel portion 9c and the beads have hence moved into the medicament container 11 such that the plunger 18 has reached its final position and all medicament contained in the medicament container 11 has been expelled through the delivery member 11a.

Figure 13:
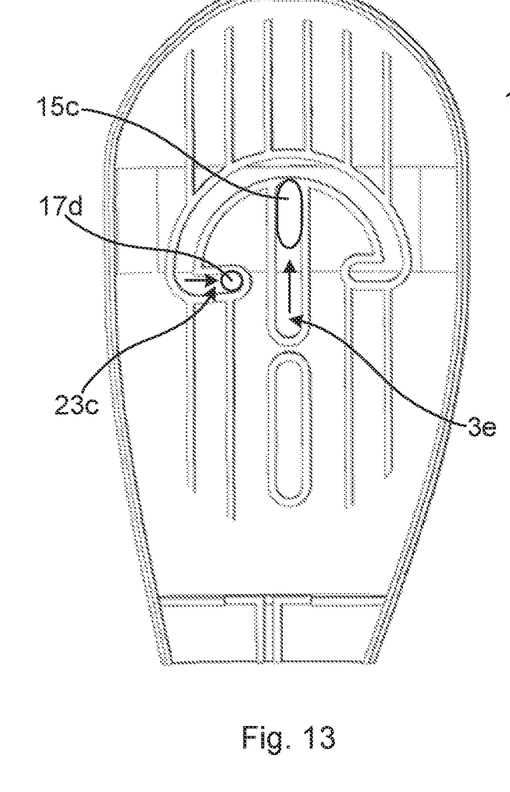
FIG. 13 depicts the positions of the first guide structure and the second guide structure during auto-withdrawal of the delivery member.

In FIG. 13, in a phase C) due to the continued actuation of the rotator housing 17 by the rotation device, the second guide structure 17d moves into and along the second straight portion 23c away from the arced portion 23a. The first guide structure 15c is therefore moved from the temporary position in the distal direction along the first track 3e to the initial position. The rotator base member 15, the rotator housing 17, the rotator housing cover 19, and the medicament container carrier 9 are therefore moved in the distal direction. The medicament container 11 is hence moved in the distal direction and the delivery member 11a is moved back into the housing 3. Auto-withdrawal functionality is thereby provided. It may hence be ensured that the delivery member 11a will not be exposed after medicament delivery.

Figure 14:
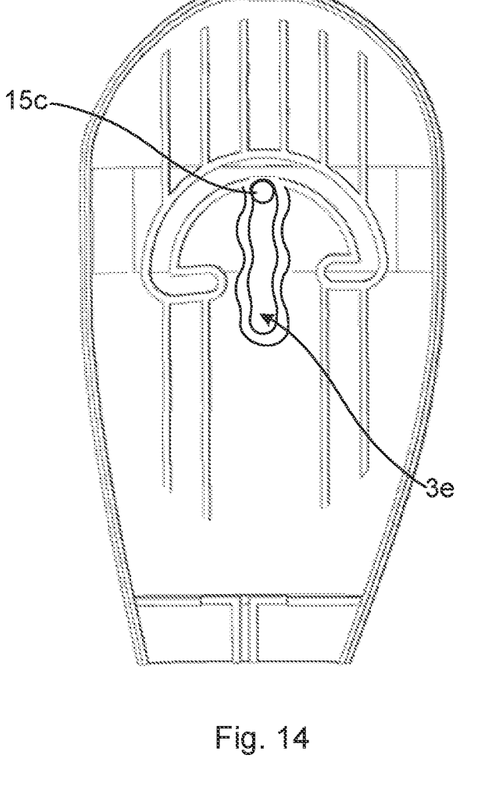
FIG. 14 shows a variation of the base member.

FIG. 14 shows a variation of the base member 3a comprising a first track 3e that is elongated but not straight. The first track 3e is in this example undulating but could alternatively or additionally for example be slightly curved.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A drive mechanism for a medicament delivery device, comprising:
   a base member having a guide track structure, the guide track structure including a first track and a second track, wherein the second track has an arced portion, a first straight portion, and a second straight portion;
   a rotator base member having a first guide structure configured to run in the first track;
   a rotator housing coaxially arranged with and configured to engage with the rotator base member, the rotator housing having a second guide structure arranged at a fixed distance from the first guide structure and configured to run in the second track;
   a rotation device configured to actuate the rotator housing; and
   a medicament container carrier configured to receive a medicament container, wherein the medicament container carrier is coaxially arranged relative to the rotator base member and the rotator housing, the rotator housing being configured to rotate relative to the medicament container carrier,
   wherein the first track and the second track are arranged relative to each other such that actuation of the rotator housing causes the second guide structure to move along the second track and the first guide structure to initially move in a first direction along the first track and subsequently to move in a second direction opposite to the first direction,
   wherein the movement in the first direction causes initial linear movement of the medicament container carrier in the first direction,
   wherein the movement in the second direction causes subsequent movement of the medicament container carrier in the second direction, and
   wherein movement of the second guide structure causes rotation of the rotator housing, thereby enabling a medicament delivery.

2. The drive mechanism as claimed in claim 1, wherein the arced portion connects the first straight portion and the second straight portion,
   wherein the first track and the second track are arranged relative to each other such that said movement of the second guide structure along the second track comprises three phases A, B, and C,
   wherein phase A comprises when the first guide structure is moved in the first direction from an initial position to a temporary position along the first track, the second guide structure is configured to move along the first straight portion towards the arced portion, wherein phase B comprises when the second guide structure reaches the arced portion, the second guide structure is configured to move along the arced portion towards the second straight portion, wherein the first guide structure maintains its temporary position, causing rotation of the rotator housing, and wherein phase C comprises when the second guide structure reaches the second straight portion, the first guide structure is configured to move in the second direction from the temporary position to the initial position along the first track and the second guide structure is configured to move along the second straight portion away from the arced portion, causing the medicament container carrier to move in the second direction.

3. The drive mechanism as claimed in claim 1, wherein the base member has a proximal end and a distal end and a central longitudinal axis extending between the proximal end and the distal end, wherein the first track extends parallel with the central longitudinal axis.

4. The drive mechanism as claimed in claim 1, wherein the first straight portion and the second straight portion extend radially inwards from the arced portion, the first straight portion and the second straight portion being arranged opposite to each other.

5. The drive mechanism as claimed in claim 2, wherein the arced portion is arranged distally relative to the first track, partially enclosing the first track, wherein the first straight portion and the second straight portion extend towards the first track from opposing sides.

6. The drive mechanism as claimed in claim 1, wherein the first track and the second track are disjoint tracks.

7. The drive mechanism as claimed in claim 1, wherein the rotation device is a clock spring.

8. The drive mechanism as claimed in claim 7, comprising a movable trigger mechanism, wherein in an initial state of the drive mechanism, the trigger mechanism is configured to prevent the rotation device from rotating the rotator housing.

9. The drive mechanism as claimed in claim 8, wherein movement of the trigger mechanism is configured to release the rotator housing, enabling the rotator housing to be actuated by the rotation device.

10. The drive mechanism as claimed in claim 1, wherein the rotation device comprises a motor and a planetary gear train configured to actuate the rotator housing.

11. The drive mechanism as claimed in claim 1, comprising a plurality of beads, wherein the medicament container carrier has a channel having a straight channel portion and a curved channel portion leading into the straight channel portion, the straight channel portion being configured to receive a medicament container, the beads being arranged one after another in the curved channel portion.

12. The drive mechanism as claimed in claim 11, wherein the rotator housing has a protrusion extending into the curved channel portion and arranged at one end of the beads, wherein rotation of the rotator housing relative to the medicament container carrier causes the protrusion to move the beads in the curved channel portion into the straight channel portion.

13. A medicament delivery device comprising the drive mechanism as claimed in claim 1.

14. The medicament delivery device as claimed in claim 13, wherein the base member forms a first housing part of the medicament delivery device.

15. The medicament delivery device as claimed in claim 13, comprising a pre-filled medicament container with a medicament delivery member covered by a protective delivery member shield and a cap with a delivery member shield remover.

16. A drive mechanism for a medicament delivery device, comprising:
- a base member comprising a first track and a second track that are configured as disjoint tracks;
- a rotator base member comprising a first guide structure that runs in the first track;
- a rotator housing coaxially arranged with and configured to engage with the rotator base member, where the rotator housing comprises a second guide structure that runs in the second track; and
- a medicament container carrier coaxially arranged relative to the rotator base member and the rotator housing, where the rotator housing rotates relative to the medicament container carrier, wherein the first track and the second track are arranged relative to each other such that movement of the rotator housing causes the second guide structure to move along the second track and the first guide structure to initially move in a first direction along the first track and to subsequently move in a second direction opposite to the first direction, wherein the movement of the first and second guide structures in the first direction causes initial linear movement of the medicament container carrier in the first direction, wherein the movement of the first and second guide structures in the second direction causes subsequent movement of the medicament container carrier in the second direction, wherein movement of the second guide structure causes rotation of the rotator housing and medicament delivery, and wherein the second track has an arced portion, a first straight portion, and a second straight portion.

17. The drive mechanism of claim 16, wherein the arced portion connects the first straight portion and the second straight portion.

18. The drive mechanism of claim 16, wherein the first track and the second track are arranged relative to each other such that said movement of the second guide structure along the second track has three distinct phases comprising:

phase A, where when the first guide structure is moved in the first direction from an initial position to a temporary position along the first track, the second guide structure moves along the first straight portion towards the arced portion;

phase B, where when the second guide structure reaches the arced portion, the second guide structure is moves along the arced portion towards the second straight portion, wherein the first guide structure maintains its temporary position, causing rotation of the rotator housing; and phase C, where when the second guide structure reaches the second straight portion, the first guide structure moves in the second direction from the temporary position to the initial position along the first track and the second guide structure moves along the second straight portion away from the arced portion, causing the medicament container carrier to move in the second direction.

19. The drive mechanism of claim 16 further comprising a clock spring that rotates the rotator housing and comprising a pre-filled medicament container positioned with the medicament container carrier.

20. The drive mechanism of claim 19 further comprising a movable trigger mechanism, wherein in an initial state of the drive mechanism, the trigger mechanism prevents the clock spring from rotating the rotator housing.

\* \* \* \* \*